United States Patent [19]

Nietupski et al.

[11] Patent Number: 5,705,339
[45] Date of Patent: Jan. 6, 1998

[54] METHODS FOR THE DETECTION OF THE BACTERIAL AGENTS CAUSING SPOILAGE OF BEER

[75] Inventors: Raymond M. Nietupski, Millbury; Benjamin B. Stone, Holliston; William G. Weisburg, Milford, all of Mass.

[73] Assignee: Amoco Corporation, Chicago, Ill.

[21] Appl. No.: 455,063

[22] Filed: May 31, 1995

Related U.S. Application Data

[62] Division of Ser. No. 121,053, Sep. 10, 1993, Pat. No. 5,484,909.
[51] Int. Cl.$^6$ ..................................... C12Q 1/68
[52] U.S. Cl. ............................ 435/6; 435/252.9
[58] Field of Search ............... 435/6, 252.9; 536/23.1, 536/23.7, 24.3, 24.32

[56] References Cited

U.S. PATENT DOCUMENTS

| 5,087,558 | 2/1992 | Webster, Jr. | 435/5 |
| 5,484,909 | 1/1996 | Nietupski et al. | 536/24.32 |

OTHER PUBLICATIONS

Hertel et al., System. Appl. Microbiol., 14, 173–177, 1991.
Woese et al., Genbank, Accession No. M58824, Dec. 23, 1991.

*Primary Examiner*—Scott W. Houtteman
*Attorney, Agent, or Firm*—Norval B. Galloway

[57] ABSTRACT

Nucleic acid sequences which preferentially bind to the rRNA or rDNA of microorganisms which cause the spoilage of beer are disclosed. The beer spoilage microorganisms are predominantly of the genera Lactobacillus and Pediococcus. The nucleic acids may be used as probes in assays to detect the presence of these microorganisms. Kits containing two or more probes are also described.

16 Claims, 1 Drawing Sheet

METHODS FOR THE DETECTION OF THE BACTERIAL AGENTS CAUSING SPOILAGE OF BEER

This application is a divisional of application Ser. No. 08/121,053, filed Sep. 10, 1993, now U.S. Pat. No. 5,484,909.

This invention relates to nucleic acids, probes, kits, and methods for the detection of organisms, including Pediococcus sp. and Lactobacillus sp. which are involved with the spoilage of beer in the brewing environment.

BACKGROUND OF THE INVENTION

The prevention of beer-spoilage by contaminating microorganisms is a major concern of commercial breweries. The predominant organisms which have been shown to spoil beer, or which have been associated with beer-spoilage are members of the genera Lactobacillus and Pediococcus (see *The Prokaryotes*, Vol. II, 2nd Edition, Balows, et al, Eds., 1991). These bacteria may be present in very low numbers and their detection may require three to five days or more by traditional culture methods.

Members of the genus Pediococcus are Gram-positive cocci which frequently form tetrads. They have complex nutritional requirements and are capable of fermenting a variety of sugars. They are facultative anaerobes found in a variety of habitats, most frequently associated with fermenting vegetation. There are eight species in this genus; *P. damnosus* is the primary member of the genus known to cause beer spoilage.

The genus Lactobacillus contains Gram-positive nonsporulating rods, utilizing strictly fermentative metabolism and having complex nutritional requirements. They are found in a variety of habitats, including water, dairy, meat and fish products, vegetation and fermenting vegetation, and in the mouth and intestinal tract of mammals.

Several studies have identified bacterial strains capable of spoiling beer, and the relative numbers of strains within the species so implicated were, in decreasing order of importance: *Lactobacillus brevis, P. damnosus, L. casei, L. lindneri, L. coryniformis, L. buchneri, L. plantarum,* and *L. curvatus*.

The current methods of detection of beer-spoilage organisms rely on classical microbiology and a general determination of the presence or absence of contamination by bacteria. These methods include: (a) culture, (b) direct fluorescence antibody (DFA), and (c) nucleic acid probes for culture confirmation. Actual identification of spoilage organisms requires classical biochemical tests and fulfillment of Koch's postulates, i.e. "reinfecting" fresh beer and showing it to become spoiled.

DESCRIPTION OF THE INVENTION

One aspect of this invention is to provide nucleic acids complementary to unique nucleic acid sequences within the ribosomal RNA (rRNA) and DNA (rDNA) of organisms which cause beer spoilage, but are not present in unspoiled beer. It is another aspect of this invention to provide nucleic acid probes which can hybridize to target regions which can be rendered accessible to probes under normal assay conditions. It is a further aspect of the invention to provide for probes which either (1) specifically discriminate between *P. damnosus* and non-Pediococcus species; (2) specifically discriminate between the majority of Pediococcus strains causing beer-spoilage and other species; (3) specifically discriminate between *L. brevis* and non-Lactobacillus species; (4) specifically discriminate between a cluster of Lactobacillus species (the cluster being a group of bacteria consisting of *L. fructivorans, L. casei, L. curvatus, L. brevis,* and *L. buchneri*) and non-cluster species; (5) specifically discriminate between the group of *P. damnosus* and *L. brevis* and other species; (6) specifically discriminate between the majority of Pediococcus and Lactobacillus species causing beer spoilage and other species; or (7) specifically discriminate between the majority of Pediococcus and Lacrobacillus (and related species) and other species.

Bacterial ribosomes contain three distinct RNA molecules which, at least in *Escherichia coli* are referred to as 5S, 16S, and 23S rRNAs. In eukaryotic organisms, there are four distinct rRNA species, generally referred to as 5S, 18S, 28S and 5.8S. These names are historically related to the size of the RNA molecules, as determined by their sedimentation rate. In actuality, however, rRNA molecules vary substantially in size between organisms. This notwithstanding,5S, 16S and 23s rRNA are art-recognized names reining to rRNA molecules in any bacteria and this convention will be used herein.

DEFINITIONS

Figure 1:
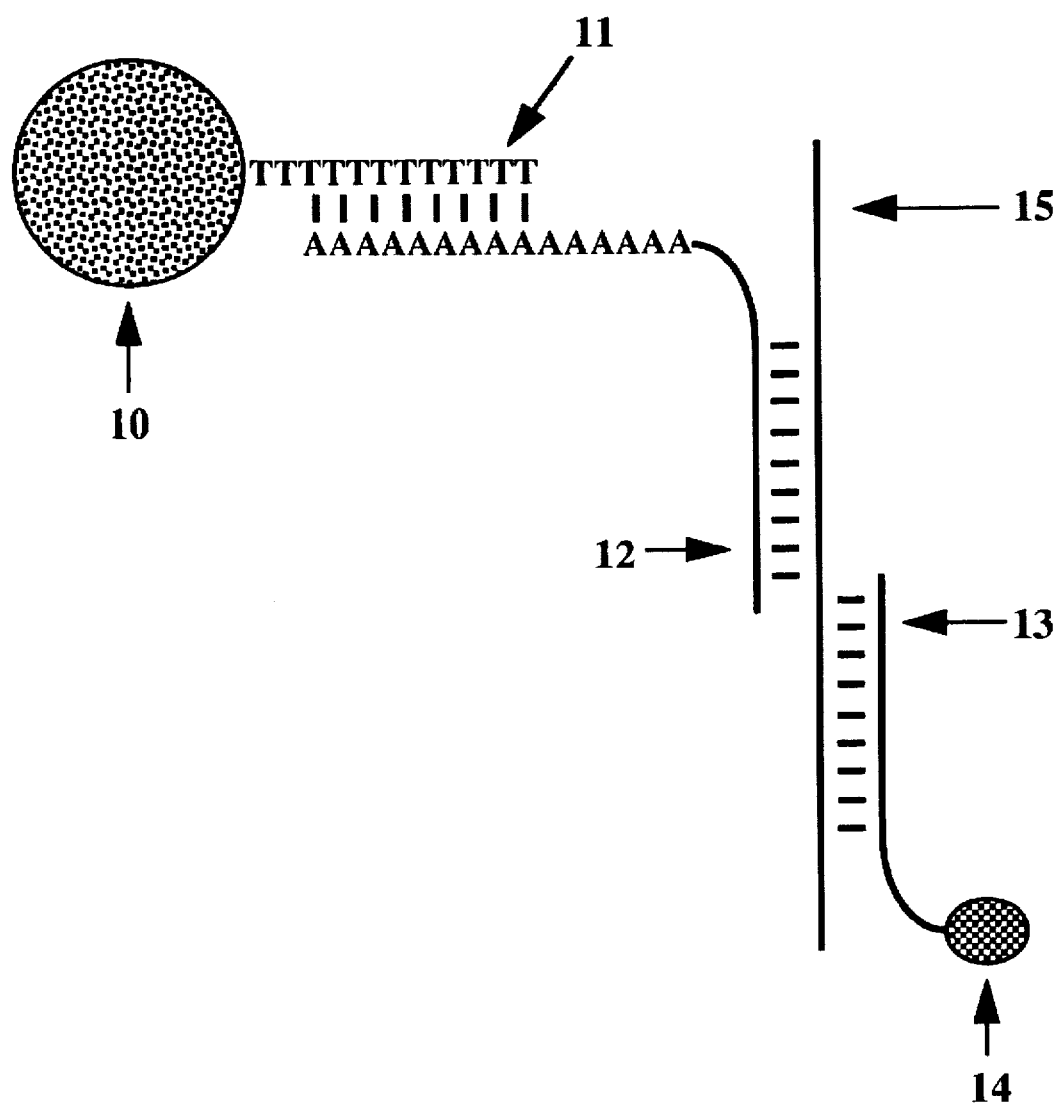
FIG. 1 is a diagram of a sandwich assay.

As used throughout the application and claims, the term "probe" will refer to synthetic or biologically produced nucleic acids, of 10 to 250 bases in length, which by design or selection, contain specific nucleotide sequences that allow specific and preferential hybridization under predetermined conditions to target nucleic acid sequences, and optionally contain a moiety for detection or enhancing assay performance. A minimum of ten nucleotides is generally necessary in order to statistically obtain specificity and form stable hybridization products, and a maximum of 250 nucleotides generally represents an upper limit of nucleotides in which reaction parameters can be adjusted to determine mismatched sequences and preferential hybridization. Therefore, in general, a preferred length of a probe will be between 10 and 250 nucleotides. Probes may also optionally contain certain constituents that pertain to their proper or optimal functioning under certain assay conditions. For example, probes may be modified to improve their resistance to nuclease degradation (such as by end-capping), to carry detection ligands (such as fluorescein, $^{32}$P, biotin, etc.) or to facilitate their capture onto a solid support (e.g. poly-deoxyadenosine "tails").

"Preferential hybridization" or "hybridizing preferentially" is to be used in a relative sense; i.e. one hybridization reaction product is more stable than another one under identical conditions. Under some conditions, a hybridization reaction product may be formed with respect to one target, but not another potential binding partner. It is well within the skill of the ordinary artisan to compare stability of hybridization reaction products and evaluate which one is more stable, i.e. determine which one has bound "preferentially".

As used herein, the terms "homology" and "homologous to" are meant to refer to the degree of similarity between two or more nucleic acid sequences, and is not meant to imply any taxonomic relatedness between organisms. The degree of similarity is expressed as a percentage, i.e. 90% homology between two sequences will mean that 90% of the bases of the first sequence are identically matched to the bases of the second sequence.

A "cluster of Lactobacillus species" means a group of Lactobacillus species selected from the group consisting of *L. fructivorans, L. casei, L. curvatus, L. brevis,* and *L. buchneri*.

"Specific" means that a nucleotide sequence will hybridize to a defined target sequence and will substantially not hybridize to a non-target sequence, or that hybridization to a non-target sequence will be minimal.

"Hybridization" is a process by which, under predetermined reaction conditions, two partially or completely complementary strands of nucleic acid are allowed to come together in an antiparallel fashion to form a double stranded nucleic acid with specific and stable hydrogen bonds, following explicit rules pertaining to which nucleic acid bases may pair with one another.

"Substantial hybridization" means that the amount of hybridization will be to an extent that one observing the results would consider the result positive in a clinical setting. Data which is considered "background noise" is not substantial hybridization.

"Stringent hybridization conditions" mean approximately 35° C. to 65° C. in a salt solution of approximately 0.9 molar NaCl. Stringency may also be governed by such reaction parameters as the concentration and type of ionic species present in the hybridization solution, the types and concentrations of denaturing agents present, and the temperature of hybridization. Generally as hybridization conditions become more stringent, longer probes are preferred if stable hybrids are to be formed. As a rule, the stringency of the conditions under which a hybridization is to take place will dictate certain characteristics of the preferred probes to be employed. Such relationships are well understood and can be readily manipulated by those skilled in the art.

"Lactobacillus sp." refers to any member of the genus Lactobacillus, regardless of the species.

"Pediococcus sp." refers to any member of the genus Pediococcus, regardless of the species.

"Majority of" when referring to strains means more than half of the stains known or, more than half of the strains tested, when one tests a representative sampling of at least 25 strains. When referring to species, it means more than one half of the known species, or more than one half of the species tested, when one tests a representative number of species.

In accordance with this invention, there are provided nucleic acids having approximately 10 to 250 nucleotides which (1) hybridize preferentially to rRNA or rDNA of *P. damnosus* as compared to other non-Pediococcus species; (2) hybridize preferentially with the majority of Pediococcus strains causing beer-spoilage compared to other species; (3) hybridize preferentially with *L. brevis* compared to non-Lactobacillus species; (4) hybridize preferentially with a cluster of Lactobacillus species (selected from the group consisting of: *L. fructivorans, L. casei, L. curvatus, L. brevis,* and *L. buchneri*) compared to other species; (5) hybridize preferentially with the group of *P. damnosus* and *L. brevis* compared to other species; (6) hybridize preferentially with the majority of Pediococcus and Lactobacillus species causing beer spoilage as compared to other species; and (7) specifically discriminate between the majority of Pediococcus and Lactobacillus (and related species) and other species. Under those same hybridization conditions, the nucleic acids of this invention do not substantially hybridize to the rRNA or rDNA of non-target organisms, or the host or environmental matrix which may be present in test samples.

The nucleic acids of this invention are useful for detecting the presence of an organism which would cause spoilage in beer. Probes which are either complementary to or at least 90% homologous to at least ten consecutive nucleic acids of the aforementioned nucleotides also form another aspect of this invention.

One embodiment of this invention are nucleic acids and probes which are homologous to or hybridize to regions of 16S rRNA or rDNA of beer-spoiling microorganisms. The regions of 16S rRNA of particular interest are in reference to the numbering of the homologous regions in *E. coli*, a standard well known to those of ordinary skill in the art, include:

*P. damnosus:* 16S rRNA positions 285 to 320, 450 to 485, and 1435 to 1470;

*L. brevis:* 16S rRNA positions 75 to 105, and 450 to 485;

*P. damnosus* or *L. brevis:* 16S rRNA position 805 to 840;

Pediococcus and Lactobacillus: 16S rRNA positions 120 to 150, 210 to 245, 280 to 315, 485 to 515, and 750 to 785.

Another embodiment of this invention is nucleic acids and probes which hybridize to regions of 23S rRNA or rDNA of beer-spoiling microorganisms. The regions of 23S rRNA of particular interest are in reference to the numbering of the homologous regions in *E. coli*, a standard well known to those of ordinary skill in the art, include:

*P. damnosus* 23S rRNA positions 700 to 740, 870 to 910, 925 to 960, 1130 to 1165, and 1205 to 1245.

*L. brevis* 23S rRNA positions 280 to 320, 325 to 363, 1130 to 1165, 1265 to 1300 and 1480 to 1512.

*P. damnosus* and *L. brevis* 23S rRNA positions 600 to 635.

Preferably the nucleic acid composition is complementary to or homologous with at least 90% of a sequence comprising any ten consecutive nucleotides within sequences selected from the group of sequences defined by the group of probes consisting of: 2858, 2861, 2867, 2876, 2877, 2868, 2869, 2880, 2891, 2892, 2895, 2899, 2904, 2896, 2873, 2881, 2887, 2875, 2901, 2854, 2879, and 2902. The sequences of these probes are presented below.

A further embodiment of this invention includes a kit for the detection of the presence of beer-spoiling microorganisms. The kit comprises a set of nucleic acids comprising at least two nucleic acids. Each nucleic acid is of 10 to 250 nucleotides and is of a different base sequence composition. Each nucleic acid is complementary to or homologous with at least 90% of a sequence comprising any ten consecutive nucleotides selected from the group of sequences defined by probes 2858, 2861, 2867, 2876, 2877, 2868, 2869, 2880, 2891, 2892, 2895, 2899, 2904, 2896, 2873, 2881, 2887, 2875, 2901, 2854, 2879, and 2902. A set of nucleic acids is particularly suited for detecting beer-spoiling microorganisms in a two probe, sandwich assay. The kit additionally comprises reagents, compositions, instructions, disposable hardware and suitable packaging to allow marketing in a convenient assembly.

A further embodiment of the present invention includes methods for the detection of the presence of beer-spoiling microorganisms. The method comprises the steps of contacting a sample suspected of containing a target with at least one nucleic acid. The nucleic acid has approximately 10 to 250 nucleotides which hybridize preferentially to rRNA or rDNA of: (1) *P. damnosus*; (2) the majority of Pediococcus strains causing beer-spoilage, but not other species; (3) *L. brevis*, but not other Lactobacillus species; (4) a cluster of Lactobacillus species (comprised of *L. fructivorans, L. casei, L. curvatus, L. brevis,* and *L. buchneri*), but not other species; (5) the group of *P. damnosus* and *L. brevis*, but not other species; (6) the majority of Pediococcus strains and Lactobacillus species which cause beer spoilage, but not other species; and (7) the majority of Pediococcus and Lactobacillus (and related species) but not other species. The method includes the steps of imposing hybridization conditions on the sample such that the nucleic acid binds preferentially to the target rRNA or rDNA to form nucleic acid complexes and detecting the complexes as an indication of the presence of the target organism(s). Preferably, the nucleic acid of the present invention is at least 90% homologous to a sequence comprising any ten consecutive nucleotides selected from the group consisting of sequences defined by probes 2858, 2861, 2867, 2876, 2877, 2868, 2869, 2880, 2891, 2892, 2895, 2899, 2904, 2896, 2873, 2881, 2887, 2875, 2901, 2854, 2879, and 2902.

The probes of the present invention provide the basis for development of a nucleic acid hybridization assay for the specific detection of beer-spoilage organisms, in beer or in environmental samples. The probes of the present invention also form the basis for confirmation of the presence of microorganisms which have been shown to spoil beer.

The first step taken in the development of the probes of the present invention involved the identification of the regions of 16S or 23S rRNA which potentially could serve as target sites for specific nucleic acid probes with the desired sensitivity. This included discovering which probe target sites were unique to: 1) *P. damnosus;* 2) the majority of Pediococcus strains causing beer-spoilage; 3) *L. brevis;* 4) a subgroup of the Lactobacillus sp.; 5) the group of *P. damnosus* and *L. brevis;* 6) the group of the majority of Pediococcus and Lactobacillus species which have been shown to spoil beer; and 7) the group of the majority of Pediococcus and Lactobacillus and related species. This involved finding sites which are:

1. different between *P. damnosus* and other Pediococcus and non-Pediococcus species;
2. different between the majority of Pediococcus strains tested and other species;
3. different between *L. brevis* and other Lactobacillus and non-Lactobacillus species;
4. different between a cluster of Lactobacillus species (*L. fructivorans, L. casei, L. curvatus, L. brevis,* and *L. buchneri*) and other species;
5. different between the group of *P. damnosus* and *L. brevis* and other species;
6. similar for all organisms which have been shown to cause beer-spoilage as demonstrated by a representative sampling of 25 strains, but different between the next closest evolutionary neighbors' sequences; and
7. similar between the majority of Pediococcus and Lactobacillus and related species, but different from other species except for *L. minutus, L. lacti,* members of the Micrococcus genus and members of the Pectinatus genus.

To accomplish the above analysis, precise alignments of *P. damnosus* and *L. brevis* 16S and 23S rRNA sequences were developed. The essentially complete 16S and 23S rRNA sequences of both *P. damnosus* and *L. brevis* were determined using standard laboratory protocols. The rDNAs so obtained were cloned into plasmid vectors from products produced by enzymatic amplification (such as that described in Weisburg, 1991, *J. Bacteriol.* 173:697–703, which is incorporated herein by reference). The *P. damnosus* and *L. brevis* sequences were aligned with homologous sequences of other Lactobacillus species, Gram-positive organisms and other eubacterial rRNA sequences including *E. coli* (which are widely used as standard reference sequences by those of ordinary skill in the art).

Based on the determined 16S and 23s rRNA sequences of *P. damnosus* and *L. brevis,* twenty-two probes were designed, synthesized, and tested. The specific behaviors of the probes are dependent to a significant extent on the assay format in which they are employed. Conversely, the assay format will dictate certain of the optimal features of the particular probes.

The discovery that probes could be generated with the extraordinary inclusivity and exclusivity characteristics of the present invention with the respect to *P. damnosus* and *L. brevis* without incurring undesirable levels of cross-reactivity was unpredictable and unexpected.

The first group of preferred probes are able to differentiate between *P. damnosus* and other species.

*P. damnosus* Specific 16S rRNA Probes

*P. damnosus* Probe 2858 (28 mer, 46% G+C) (SEQ ID NO:1) 5'-TCA CAG CCT TGG TGA GCC TTT ATC TCA T-3'

*P. damnosus* Probe 2861 (29 mer, 48% G+C) (SEQ ID NO:2) 5'-CAC TGC ATG AGC AGT TAC TCT CAC ACA CT-3'

*P. damnosus* Probe 2867 (28 mer, 61% G+C) (SEQ ID NO:3) 5'-CGG CTA GCT CCC GAA GGT TAC TCC ACC T-3'

A second group of preferred probes are able to detect the majority of Pediococcus beer-spoilage strains.

Majority of Pediococcus Genus 23S rRNA Probes

Pediococcus Genus Probe 2876 (32 mer, 50% G+C) (SEQ ID NO:4) 5'-CCA CAG TCT CGG TAA TAT GTT TAA GCC CCG GT-3'

Pediococcus Genus Probe 2877 (31 mer, 58% G+C) (SEQ ID NO:5) 5'CGC TCC AAC AGT CCT CAC GGT CTG CCT TCA T-3'

A third group of preferred probes are specific for *L. brevis.*

*L. brevis* Specific 16S rRNA Probes

*L. brevis* Probe 2868 (28 mer, 43% G+C) (SEQ ID NO:6) 5'-CAA CGT CTG AAC AGT TAC TCT CAA ACG T-3'

*L. brevis* Probe 2869 (32 mer, 41% G+C) (SEQ ID NO:7) 5'-CCG ATG TTA AAA TCC GTG CAA GCA CTT CAT TT-3'

*L. brevis* Specific 23S rRNA Probes

*L. brevis* Probe 2880 (31 mer, 45% G+C) (SEQ ID NO:8) 5'-TGA GGG TTA TTG GTT TCG TTT ACG GGG CTA T-3'

*L. brevis* Probe 2891 (33 mer, 48% G+C) (SEQ ID NO:9) 5'-CAG GCT TCC CAA CCT GTT CAA CTA CCA ACA ACT-3'

*L. brevis* Probe 2892 (30 mer, 53% G+C) (SEQ ID NO:10) 5'-CCA CAA TTT GGT GGT ATC CTT AGC CCC GGT-3'

*L. brevis* Probe 2895 (32 mer, 53% G+C) (SEQ ID NO:11) 5'-CAA CCC GGC TGC CAG CAT TTA ACT GGT AAC CT-3'

A fourth group of probes is specific to a cluster of Lactobacillus species. A preferred one is given below.

Cluster of Lactobacillus sp. 23S rRNA Probe

Lactobacillus cluster Probe 2899 (32 mer, 47% G+C) (SEQ ID NO:12) 5'-TCG GTG GAT CAG ATT CTC ACT GAT CTT TCG CT-3'

A fifth group of probes can detect both *P. damnosus* and *L. brevis.* Preferred ones are given below.

*P. damnosus* and *L. brevis* 16S rRNA Probes

*P. damnosus* and *L. brevis* Probe 2904 (30 mer, 43% G+C) (SEQ ID NO:13) 5'-CCA ACA CTT AGC ATT CAT CGT TTA CGG CAT-3'

*P. damnosus* and *L. brevis* 23S rRNA Probes

*P. damnosus* and *L. brevis* Probe 2896 (32 mer, 44% G+C) (SEQ ID NO:14) 5'-TTC GCT ACG GCT CCG TTT TTT CAA CTT AAC CT-3'

A sixth group of probes hybridizes with the majority of Pediococcus and Lactobacillus species, and all beer-spoilage organisms. Preferred ones are given below.

16S rRNA Beer-Spoilage Organism Probes

Beer-spoilage organism Probe 2873 (28 mer, 64% G+C) (SEQ ID NO:15) 5'-CCC CTG CTT CTG GGC AGG TTA CCC ACG T-3'

Beer-spoilage organism Probe 2881 (28 mer, 57% G+C) (SEQ ID NO:16) 5'-TCG CTA CCC ATG CTT TCG AGC CTC AGC T-3'

Beer-spoilage organism Probe 2887 (30 mer, 63% G+C) (SEQ ID NO:17) 5'-CGC CGC GGG TCC ATC CAG AAG TGA TAG CCT-3'

23s rRNA Beer-Spoilage Organism Probes

Beer-spoilage organism Probe 2875 (32 mer, 50% G+C) (SEQ ID NO:18) 5' CTG AAT TCA GTA ACC CTA GAT GGG CCC CTA GT-3'

Beer-spoilage organism Probe 2901 (32 mer, 44% G+C) (SEQ ID NO:19) 5'-TAT CAC TCA CCG TCT GAC TCC CGG ATA TAA AT-3'

A seventh group of probes will hybridize to the majority of Pediococcus and Lactobacillus species. Preferred ones are presented below.

Majority of Pediococcus and Lactobacillus species 16S rRNA Probes

Pediococcus/Lactobacillus Probe 2854 (27 mer, 48% G+C) (SEQ ID NO:20) 5'-TAG TTA GCC GTG GCT TTC TGG TTG GAT-3'

Pediococcus/Lactobacillus Probe 2879 (28 mer, 54% G+C) (SEQ ID NO:21) 5'-CGA TTA CCC TCT CAG GTC GGC TAC GTA T-3'

Majority of Pediococcus and Lactobacillus species 23S rRNA Probes

Pediococcus/Lactobacillus Probe 2902 (31 mer, 58% G+C) (SEQ ID NO:22) 5'-TTC GGG CCT CCA GTG CGT TTT ACC GCA CCT T-3'

The probes of the present invention may be used in a "sandwich" assay. As shown in FIG. 1, the "sandwich" assay involves use of a pair of probes simultaneously. One probe, designated the "capture" probe 12 is a bifunctional nucleotide made by adding a homopolymeric 3' tail to a probe with preferably high target specificity. The tail will hybridize to the complementary homopolymer 11 on a solid surface 10, such as a glass bead or a filter disc. Hybridization of the capture probe 12 to its target 15, in this case Pediococcus/Lactobacillus rRNA, would complex the target 15 with the solid support 10. The detector probe 13, preferably with some degree of specificity, would be a part of a detection scheme which may use virtually any sort of detection moiety 14, including radioactivity, fluorescence, chemiluminescence, color or other detector moiety. The detector probe may be incorporated as an RNA sequence into an amplifiable Q-beta midivariant as described by Kramer and Lizardi, 1989 Nature 339.

A sample, such as a swab or liquid aliquot is processed as to liberate the total nucleic acid content. The sample, putatively containing disrupted beer-spoilage organisms, is incubated in the presence of a capture probe, detector probe, and magnetic particle beads which have been derivatized with oligo-deoxyThymidine in a chaotropic buffer such as guanidinium isothiocyanate.

If target molecules (beer-spoilage microorganisms of the genus Pediococcus or Lactobacillus) are present, a Bead-Capture Probe-Target-Detector Probe hybridization complex is formed, as in FIG. 1. The presence of a magnet near the bottom of the reaction tube will cause the magnetic particle-hybridization complex to adhere to the side of the tube, enabling the removal of the sample matrix, unbound probe, and other constituents not hybridized. Repeated rehydration and denaturation of the Bead-Capture Probe-Target-Detector Probe complex would enable significant background reduction. The final detection may involve spotting the beads on a membrane and assaying by an appropriate method, such as autoradiography, if the detector probe was labelled with a radioisotope. Alternatively, the detector probe may be an amplifiable midivariant probe.

The following non-limiting Examples are presented to better illustrate the invention.

EXAMPLE 1

Dot-Blot Analysis of Probe Hybridization Behavior

Dot-blot analysis, in accordance with well-known procedures, involves immobilizing a nucleic acid or a population of nucleic acids on a filter such as nitrocellulose, nylon or other derivatized membranes which can be readily obtained commercially. Either DNA or RNA can be so immobilized and subsequently tested for hybridization under a variety of conditions (stringencies) with nucleotide sequences or probes of interest. Under stringent conditions, probes with nucleotide sequences with greater complementarity to the target will exhibit a higher level of hybridization than probes whose sequences have less homology.

Probes of the present invention are tested in a dot-blot. One hundred nanograms RNA, is purified by phenol extraction and centrifugation through cesium trifluoroacetate gradients, denatured and spotted on a nylon membrane. Probes are isotopically labelled with the addition of a $^{32}$P-Phosphorous moiety to the 5' end of the oligonucleotide by the established polynucleotide kinase reaction. Hybridization of the probes is conducted at a temperature of 60° C. in the presence of 1.08M NaCl, 60 mM sodium phosphate and 6 mM ethylenediamine tetraacetic acid (EDTA), pH 7.4. Unhybridized probe is removed by washing at a salt concentration of one-third of the hybridization condition. The filters are exposed to X-ray film and the intensity of the hybridization signals is evaluated after three hours of autoradiographic exposure.

The following TABLE 1 is a summary of results.

*P. damnosus* probes targeting 16S rRNA

Probe 2858: All *P. damnosus* strains

Probe 2861: All *P. damnosus* strains; one isolate of Lactobacillus.

Probe 2867: All *P. damnosus* strains

*L. brevis* probes targeting the 16S rRNA

Probe 2868: *L. brevis* specific. This probe misses some isolates identified as *L. brevis*, but this is thought to be to inaccurate identification of some environmental isolates.

Probe 2869: *L. brevis* specific.

Group of *P. damnosus* and *L. brevis* probes targeting the 16S rRNA

Probe 2904: *P. damnosus* and *L. brevis*. Also detects *L. buchneri* and other related species of Lactobacillus.

All beer-spoilage organisms targeting 16S rRNA

Probe 2873: Majority of Pediococcus and Lactobacillus strains; all but one spoilage isolate.

Probe 2881: Majority of Pediococcus and Lactobacillus strains. Also detects many Gram-positive eubacteria.

Probe 2887: Majority of Pediococcus and Lactobacillus strains, all spoilage isolates.

Group of Majority of Pediococcus and Lactobacillus species probes, targeting 16S rRNA Probe 2854: Majority of Pediococcus and Lactobacillus strains, also two Bacillus species.

Probe 2879: Majority of Pediococcus and Lactobacillus strains. Also detects some Gram-positive bacteria.

Group of Majority of Pediococcus beer-spoilage organisms, probes targeting the 23S rRNA Probe 2876: Most Pediococcus strains. Also detects some Lactobacillus isolates.
Probe 2877: Most Pediococcus strains. Also detects some Lactobacillus isolates.

L. brevis probes targeting the 23S rRNA

Probe 2880: L. brevis specific. Misses some isolates identified as L. brevis, but this may be due to inaccurate identification of some environmental isolates.
Probe 2891: L. brevis specific.
Probe 2892: L. brevis specific.
Probe 2895 L. brevis specific.

Subgroup of Lactobacillus genus probes targeting 23S rRNA

Probe 2899: Most Lactobacillus species. Possibly some Pediococcus strains.

Group of P. damnosus and L. brevis probes targeting 23S rRNA

Probe 2896: P. damnosus and L. brevis. Also detects a few other species of Lactobacillus All beer-spoilage organisms targeting 23S rRNA Probe 2875: Majority of Pediococcus and Lactobacillus strains, misses some spoilage isolates.
Probe 2901: Majority of Pediococcus and Lactobacillus strains, misses some spoilage isolates.

Group of Majority of Pediococcus strains and Lactobacillus species, targeting 23S rRNA Probe 2902: Majority of Pediococcus and Lactobacillus strains. Also some Gram-positive eubacteria.

The results of the dot blot assay are presented below as TABLE 2. In this table, ++++ indicates the strongest signals observed; +++ indicates strong signal observed; ++ indicates a somewhat weaker, but definitely positive hybridization signal observed; + indicates a weak signal; +− indicates a very weak, barely detectable signal; − indicates no signal observed. ND indicates that this assay was not performed. If a probe binds strongly (either ++++ or +++) to at least one target, but exhibits a weak hybridization (+ or +−) to a second target, the probe is considered to substantially hybridize only with the targets giving the ++++ or+++ results.

TABLE 2

Pediococcus and Lactobacillus Dot Blot Hybridization Results

| Probe Organism | Designation | 2858 | 2861 | 2867 | 1660 Eubacterial |
|---|---|---|---|---|---|
| | | Pediococcus damnosus 16S | | | |
| Pediococcus damnosus | P2 | ++++ | ++++ | ++++ | ++++ |
| P. damnosus | P5 | ++++ | ++++ | ++++ | ++++ |
| P. damnosus | P10 | ++++ | ++++ | ++++ | ++++ |
| P. damnosus | P17 | ++++ | ++++ | ++++ | ++++ |
| P. damnosus | ATCC29358 | ++++ | ++++ | ++++ | ++++ |
| P. pentosaceus | ATCC33316 | + | − | − | ++++ |
| P. pentosaceus var. intermedius | P18 | − | − | − | ++++ |
| Pediococcus sp. | P140 | − | − | − | ++++ |
| Pediococcus sp. | P160 | − | − | + | ++++ |
| Pediococcus sp. | P167 | − | − | − | ++++ |
| Pediococcus sp. | P172 | − | − | − | ++++ |
| Lactobacillus delbrueckii | L4 | − | − | − | ++++ |
| L. fructivorans | L9 | − | − | − | ++++ |
| L. casei | L14 | − | − | − | ++++ |
| L. delbrueckii | L17 | − | − | − | ++++ |
| L. fructivorans | L19 | − | − | − | ++++ |
| L. curvatus | L20 | − | − | − | ++++ |
| L. casei | L22 | − | − | − | ++++ |
| Lactobacillus sp. | L137 | − | − | − | ++++ |
| Lactobacillus sp. | L174 | − | − | − | ++++ |
| Lactobacillus sp. | L176 | − | − | − | ++++ |
| Lactobacillus sp. | L177 | − | − | − | ++++ |
| Lactobacillus sp. | L178 | − | − | − | +++ |
| Lactobacillus sp. | L179 | − | − | − | +++ |
| Lactobacillus sp. | L185 | − | − | − | +++ |
| Lactobacillus sp. | L193 | − | − | − | +++ |
| Lactobacillus sp. | L194 | + | − | + | ++++ |
| Spoilage isolate 1 | PedioC4908 | ND | − | ND | ++++ |
| Spoilage isolate 2 | Pedio53454 | ND | − | ND | ++++ |
| Spoilage isolate 3 | PedioC30655 | ND | ++++ | ND | ++++ |
| Spoilage isolate 4 | PedioC3303F | ND | − | ND | ++++ |
| Spoilage isolate 5 | Pedio6667 | ND | − | ND | ++++ |
| Spoilage isolate 7 | B6665 | ND | − | ND | ++++ |
| Spoilage isolate 8 | LactoC5884B | ND | − | ND | ++++ |
| Spoilage isolate 9 | Lacto53453 | ND | − | ND | ++++ |
| Spoilage isolate 11 | LactoC5884A | ND | − | ND | +++ |
| Spoilage isolate 13 | LactoC5162 | ND | − | ND | ++++ |

TABLE 2-continued

Pediococcus and Lactobacillus Dot Blot Hybridization Results

| | | | | | |
|---|---|---|---|---|---|
| Spoilage isolate 14 | C4908 | ND | – | ND | ++++ |
| Spoilage isolate 15 | LactoC3325 | ND | – | ND | ++++ |
| Spoilage isolate 10 | Lacto small | ND | – | ND | ++++ |
| Spoilage isolate 12 | Lacto large | ND | – | ND | ++++ |
| Spoilage isolate D | L. brevis GT4696 | ND | – | ND | ++++ |
| Spoilage isolate A | L. casei GT4697 | ND | – | ND | ++++ |
| Spoilage isolate F | L. brevis GT4698 | ND | – | ND | ++++ |
| Spoilage isolate B | L. casei GT4699 | ND | – | ND | ++++ |
| Spoilage isolate | L. brevis GT4700 | ND | – | ND | ++++ |
| Spoilage isolate J | L. brevis GT4702 | ND | – | ND | ++++ |
| Spoilage isolate J | L. brevis GT4703 | ND | – | ND | ++++ |
| Spoilage isolate | L. brevis GT4704 | ND | – | ND | ++++ |
| Spoilage isolate | L. delbrueckii GT4705 | ND | – | ND | ++++ |
| Spoilage isolate 852 | L. fructivorans | ND | – | ND | ++++ |
| Spoilage isolate 853 | L. fructivorans | ND | – | ND | ++++ |
| L. acidophilus | ATCC4356 | – | – | – | ++++ |
| L. brevis | ATCC8291 | – | – | – | ++++ |
| L. buchneri | ATCC11305 | – | – | – | ++++ |
| L. casei | ATCC393 | – | – | – | ++++ |
| L. casei ssp. rhamnosus | ATCC7469 | – | – | – | ++++ |
| L. delbrueckii ssp. bulgaricus | ATCC11842 | – | – | – | ++++ |
| L. fermentum | ATCC9338 | – | – | – | ++++ |
| L. minutus | ATCC33267 | – | – | – | +++ |
| L. plantarum | ATCC8014 | – | – | – | +++ |
| L. plantarum | ATCC14917 | – | – | – | +++ |
| Leuconostoc sp. | Leuco192 | – | – | – | +++ |
| Leuco. mesenteroides | ATCC8293 | – | – | – | +++ |
| Acetobacter aceti | ATCC15973 | – | – | – | ++++ |
| Acetobacter aceti | ATCC23746 | – | – | – | +++ |
| Acetobacter aceti | ATCC23747 | – | – | – | +++ |
| Acetobacter aceti | ATCC23748 | – | – | – | +++ |
| Aceto. hansenii | ATCC35959 | – | – | – | ++++ |
| Aceto. liqufaciens | ATCC14835 | ND | ND | ND | ND |
| Aceto. pasteurianus | ATCC12877 | – | – | – | ++++ |
| Aceto. pasteurianus | ATCC12879 | – | – | – | +++ |
| Aceto. pasteurianus | ATCC23650 | – | – | – | +++ |
| Aceto. pasteurianus | ATCC23758 | – | – | – | +++ |
| Aceto. pasteurianus | ATCC23764 | – | – | – | +++ |
| Aceto. pasteurianus | ATCC23765 | – | – | – | ++++ |
| Aceto. pasteurianus | ATCC23766 | – | – | – | +++ |
| Aceto. pasteurianus | ATCC23767 | – | – | – | +++ |
| Aceto. pasteurianus | ATCC33445 | – | – | – | +++ |
| Bacillus coagulans | ATCC7050 | – | – | – | ++++ |
| B. stearothermophilus | ATCC12980 | ND | ND | ND | ND |
| B. subtilis | ATCC21556 | – | – | – | ++++ |
| Citrobacter freundii | ATCC8090 | – | – | – | ++++ |
| Enterobacter aerogenes | ATCC13048 | – | – | – | +++ |
| E. agglomerans | ATCC27155 | – | – | – | +++ |
| E. cloacae | ATCC13047 | – | – | – | +++ |
| Flavobacterium ferrugineum | ATCC13524 | – | – | – | +++ |
| Gluconobacter oxydans | ATCC11894 | – | – | – | ++++ |
| G. oxydans | ATCC19357 | – | – | – | +++ |
| G. oxydans | ATCC23755 | – | – | – | +++ |
| G. oxydans | ATCC33446 | – | – | – | +++ |
| G. oxydans | ATCC33447 | – | – | – | ++++ |
| Hafnia alvei | ATCC13337 | – | – | – | ++++ |
| Klebsiella oxytoca | ATCC13182 | – | – | – | ++++ |
| Kleb. terrigena | ATCC33257 | – | – | – | ++++ |
| Lactococcus lactis ssp. lactis | ATCC19435 | + | – | – | ++++ |
| Megasphaera cerevisiae | ATCC43236 | ND | ND | ND | ND |
| Megasphaera cerevisiae | ATCC43254 | ND | ND | ND | ND |
| Micrococcus kristinae | ATCC27570 | – | – | – | ++++ |
| Micrococcus varians | ATCC15306 | – | – | – | ++++ |
| Obesumbacterium proteus | ATCC12841 | – | – | – | +++ |
| Pectinatus cerevisiiphilus | ATCC29359 | – | – | – | +++ |
| Pectinatus frisingensis | ATCC33332 | – | – | – | ++++ |
| Proteus mirabilis | ATCC29906 | – | – | – | ++++ |
| Serratia marcescens | ATCC13880 | – | – | – | ++++ |
| Staphylococcus epidermidis | ATCC14990 | – | – | + | ++++ |
| Staph. saprophyticus | ATCC15305 | – | – | + | ++++ |
| Zymomonas mobilis | ATCC31821 | ND | ND | ND | ND |
| Saccharomyces cerevisiae | ATCC18824 | – | – | – | – |
| Saccharomyces cerevisiae | ATCC2341 | – | – | – | – |
| Saccharomyces cerevisiae | ATCC36902 | – | – | – | – |

TABLE 2-continued

Pediococcus and Lactobacillus Dot Blot Hybridization Results

| | | | | | | |
|---|---|---|---|---|---|---|
| Chimay | | – | – | – | – | |
| *Candida albicans* | ATCC11006 | – | – | – | – | |
| Human/CaSKi | | – | – | – | – | |
| Stool RNA | | – | – | – | ++++ | |
| Wheat germ RNA | | – | – | – | – | |

| Probe Organism | Designation | 2868 Lactobacillus 16S | 2869 | 2880 | 2891 Lactobacillus 23S | 2892 | 2895 | 2899 |
|---|---|---|---|---|---|---|---|---|
| *Pediococcus damnosus* | P2 | – | – | – | – | – | – | – |
| *P. damnosus* | P5 | – | – | – | – | – | – | – |
| *P. damnosus* | P10 | – | – | – | – | – | – | – |
| *P. damnosus* | P17 | – | – | – | – | – | – | – |
| *P. damnosus* | ATCC29358 | – | – | – | – | – | – | – |
| *P. pentosaceus* | ATCC33316 | – | – | – | – | – | – | – |
| *P. pentosaceus* var. *intermedius* | P18 | – | – | – | – | – | – | – |
| *Pediococcus* sp. | P140 | – | – | – | – | – | – | – |
| *Pediococcus* sp. | P160 | – | – | – | – | – | – | – |
| *Pediococcus* sp. | P167 | – | – | – | – | – | – | – |
| *Pediococcus* sp. | P172 | – | – | – | – | – | – | – |
| *Lactobacillus delbrueckii* | L4 | – | – | – | – | – | – | – |
| *L. fructivorans* | L9 | – | – | – | – | – | – | ++++ |
| *L. casei* | L14 | – | – | – | – | – | – | ++++ |
| *L. delbrueckii* | L17 | – | – | – | – | – | – | – |
| *L. fructivorans* | L19 | – | – | – | – | – | – | ++++ |
| *L. curvatus* | L20 | – | – | – | – | – | – | ++++ |
| *L. casei* | L22 | – | – | – | – | – | – | ++++ |
| *Lactobacillus* sp. | L137 | – | – | – | – | – | – | ++++ |
| *Lactobacillus* sp. | L174 | – | – | – | – | – | – | ++++ |
| *Lactobacillus* sp. | L176 | – | – | – | – | – | – | ++++ |
| *Lactobacillus* sp. | L177 | – | – | – | – | – | – | ++++ |
| *Lactobacillus* sp. | L178 | – | – | – | – | – | – | ++++ |
| *Lactobacillus* sp. | L179 | – | – | – | – | – | – | ++++ |
| *Lactobacillus* sp. | L185 | – | – | – | – | – | – | ++++ |
| *Lactobacillus* sp. | L193 | – | – | – | – | – | – | ++++ |
| *Lactobacillus* sp. | L194 | – | – | – | – | – | – | + |
| Spoilage isolate 1 | PedioC4908 | – | ND | – | ND | ND | ND | – |
| Spoilage isolate 2 | Pedio53454 | – | ND | – | ND | ND | ND | – |
| Spoilage isolate 3 | PedioC30655 | – | ND | – | ND | ND | ND | – |
| Spoilage isolate 4 | PedioC3303F | – | ND | – | ND | ND | ND | +++ |
| Spoilage isolate 5 | Pedio6667 | – | ND | – | ND | ND | ND | – |
| Spoilage isolate 7 | B6665 | – | ND | – | ND | ND | ND | ++++ |
| Spoilage isolate 8 | LactoC5884B | – | ND | – | ND | ND | ND | – |
| Spoilage isolate 9 | Lacto53453 | – | ND | – | ND | ND | ND | ++++ |
| Spoilage isolate 11 | LactoC5884A | – | ND | – | ND | ND | ND | ++++ |
| Spoilage isolate 13 | LactoC5162 | – | ND | – | ND | ND | ND | ++++ |
| Spoilage isolate 14 | C4908 | – | ND | – | ND | ND | ND | – |
| Spoilage isolate 15 | LactoC3325 | – | ND | – | ND | ND | ND | ++++ |
| Spoilage isolate 10 | Lacto small | – | ND | – | ND | ND | ND | ++++ |
| Spoilage isolate 12 | Lacto large | – | ND | – | ND | ND | ND | ++++ |
| Spoilage isolate D | *L. brevis* GT4696 | – | ND | – | ND | ND | ND | ++++ |
| Spoilage isolate A | *L. casei* GT4697 | – | ND | – | ND | ND | ND | ++++ |
| Spoilage isolate F | *L. brevis* GT4698 | – | ND | – | ND | ND | ND | ++++ |
| Spoilage isolate B | *L. casei* GT4699 | – | ND | – | ND | ND | ND | ++++ |
| Spoilage isolate | *L. brevis* GT4700 | – | ND | – | ND | ND | ND | – |
| Spoilage isolate J | *L. brevis* GT4702 | – | ND | – | ND | ND | ND | ++++ |
| Spoilage isolate J | *L. brevis* GT4703 | – | ND | – | ND | ND | ND | ++++ |
| Spoilage isolate | *L. brevis* GT4704 | ++++ | ND | ++++ | ND | ND | ND | ++++ |
| Spoilage isolate | *L. delbrueckii* GT4705 | – | ND | – | ND | ND | ND | +++ |
| Spoilage isolate 852 | *L. fructivorans* | – | ND | – | ND | ND | ND | ++++ |
| Spoilage isolate 853 | *L. fructivorans* | – | ND | – | ND | ND | ND | ++++ |
| *L. acidophilus* | ATCC4356 | – | – | – | – | – | – | – |
| *L. brevis* | ATCC8291 | ++++ | ++++ | ++++ | ++++ | ++++ | ++++ | +++ |
| *L. buchneri* | ATCC11305 | – | – | – | – | – | – | +++ |
| *L. casei* | ATCC393 | – | – | – | – | – | – | ++++ |
| *L. casei* ssp. *rhamnosus* | ATCC7469 | – | – | – | – | – | – | ++++ |
| *L. delbrueckii* ssp. *bulgaricus* | ATCC11842 | – | – | – | – | – | – | – |
| *L. fermentum* | ATCC9338 | – | – | – | – | – | – | – |
| *L. minutus* | ATCC33267 | – | – | – | – | – | – | – |
| *L. plantarum* | ATCC8014 | – | – | – | – | – | – | – |
| *L. plantarum* | ATCC14917 | – | – | – | – | – | – | – |
| *Leuconostoc* sp. | Leuco192 | – | – | – | – | – | – | – |
| *Leuco. mesenteroides* | ATCC8293 | – | – | – | – | – | – | – |
| *Acetobacter aceti* | ATCC15973 | – | – | – | – | – | – | – |

TABLE 2-continued

Pediococcus and Lactobacillus Dot Blot Hybridization Results

| | | | | | | | | |
|---|---|---|---|---|---|---|---|---|
| Acetobacter aceti | ATCC23746 | − | − | − | − | − | − | − |
| Acetobacter aceti | ATCC23747 | − | − | − | − | − | − | − |
| Acetobacter aceti | ATCC23748 | − | − | − | − | − | − | − |
| Aceto. hansenii | ATCC35959 | − | − | − | − | − | − | − |
| Aceto. liquifaciens | ATCC14835 | ND | ND | ND | ND | ND | ND | ND |
| Aceto. pasteurianus | ATCC12877 | − | − | − | − | − | − | − |
| Aceto. pasteurianus | ATCC12879 | − | − | − | − | − | − | − |
| Aceto. pasteurianus | ATCC23650 | − | − | − | − | − | − | − |
| Aceto. pasteurianus | ATCC23758 | − | − | − | − | − | − | − |
| Aceto. pasteurianus | ATCC23764 | − | − | − | − | − | − | − |
| Aceto. pasteurianus | ATCC23765 | − | − | − | − | − | − | − |
| Aceto. pasteurianus | ATCC23766 | − | − | − | − | − | − | − |
| Aceto. pasteurianus | ATCC23767 | − | − | − | − | − | − | − |
| Aceto. pasteurianus | ATCC33445 | − | − | − | − | − | − | − |
| Bacillus coagulans | ATCC7050 | − | − | − | − | − | − | − |
| B. stearothermophilus | ATCC12980 | ND | ND | ND | ND | ND | ND | ND |
| B. subtilis | ATCC21556 | − | − | − | − | − | − | − |
| Citrobacter freundii | ATCC8090 | − | − | − | − | − | − | − |
| Enterobacter aerogenes | ATCC13048 | − | − | − | − | − | − | − |
| E. agglomerans | ATCC27155 | − | − | − | − | − | − | − |
| E. cloacae | ATCC13047 | − | − | − | − | − | − | − |
| Flavobacterium ferrugineum | ATCC13524 | − | − | − | − | − | − | − |
| Gluconobacter oxydans | ATCC11894 | − | − | − | − | − | − | − |
| G. oxydans | ATCC19357 | − | − | − | − | − | − | − |
| G. oxydans | ATCC23755 | − | − | − | − | − | − | − |
| G. oxydans | ATCC33446 | − | − | − | − | − | − | − |
| G. oxydans | ATCC33447 | − | − | − | − | − | − | − |
| Hafnia alvei | ATCC13337 | − | − | − | − | − | − | − |
| Klebsiella oxytoca | ATCC13182 | − | − | − | − | − | − | − |
| Kleb. terrigena | ATCC33257 | − | − | − | − | − | − | − |
| Lactococcus lactis ssp. lactis | ATCC19435 | − | − | − | − | − | − | − |
| Megasphaera cerevisiae | ATCC43236 | ND | ND | ND | ND | ND | ND | ND |
| Megasphaera cerevisiae | ATCC43254 | ND | ND | ND | ND | ND | ND | ND |
| Micrococcus kristinae | ATCC27570 | − | − | − | − | − | − | − |
| Micrococcus varians | ATCC15306 | − | − | − | − | − | − | − |
| Obesumbacterium proteus | ATCC12841 | − | − | − | − | − | − | − |
| Pectinatus cerevisiiphilus | ATCC29359 | − | − | − | − | − | − | − |
| Pectinatus frisingensis | ATCC33332 | − | − | − | − | − | − | − |
| Proteus mirabilis | ATCC29906 | − | − | − | − | − | − | − |
| Serratia marcescens | ATCC13880 | − | − | − | − | − | − | − |
| Staphylococcus epidermidis | ATCC14990 | − | − | − | − | − | − | − |
| Staph. saprophyticus | ATCC15305 | − | − | − | − | − | − | − |
| Zymomonas mobilis | ATCC31821 | ND | ND | ND | ND | ND | ND | ND |
| Saccharomyces cerevisiae | ATCC18824 | − | − | − | − | − | − | − |
| Saccharomyces cerevisiae | ATCC2341 | − | − | − | − | − | − | − |
| Saccharomyces cerevisiae | ATCC36902 | − | − | − | − | − | − | − |
| Chimay | | − | − | − | − | − | − | − |
| Candida albicans | ATCC11006 | − | − | − | − | − | − | − |
| Human/CaSKi | | − | − | − | − | − | − | − |
| Stool RNA | | − | − | − | − | − | − | − |
| Wheat germ RNA | | − | − | − | − | − | − | − |

| Probe Organism | Designation | 2854 | 2873 | 2879 | 2881 | 2887 | 2904 |
|---|---|---|---|---|---|---|---|
| | | Pediococcus/Lactobacillus 16S | | | | | |
| Pediococcus damnosus | P2 | ++++ | ++++ | ++++ | ++++ | ++++ | ++++ |
| P. damnosus | P5 | ++++ | ++++ | ++++ | ++++ | ++++ | +++ |
| P. damnosus | P10 | ++++ | ++++ | ++++ | ++++ | ++++ | ++++ |
| P. damnosus | P17 | ++++ | ++++ | ++++ | ++++ | ++++ | ++++ |
| P. damnosus | ATCC29358 | ++++ | ++++ | ++++ | ++++ | ++++ | ++++ |
| P. pentosaceus | ATCC33316 | ++++ | ++++ | ++++ | ++++ | ++++ | − |
| P. pentosaceus var. intermedius | P18 | ++++ | ++++ | ++++ | ++++ | ++++ | − |
| Pediococcus sp. | P140 | ++++ | ++++ | ++++ | ++++ | ++++ | − |
| Pediococcus sp. | P160 | ++++ | ++++ | ++++ | ++++ | ++++ | − |
| Pediococcus sp. | P167 | ++++ | ++++ | ++++ | ++++ | ++++ | − |
| Pediococcus sp. | P172 | ++++ | ++++ | ++++ | ++++ | ++++ | − |
| Lactobacillus delbrueckii | L4 | − | ++++ | ++++ | ++++ | ++++ | − |
| L. fructivorans | L9 | ++++ | | ++++ | ++++ | ++ | ++ |
| L. casei | L14 | ++++ | + | − | ++++ | +++ | ++ |
| L. delbrueckii | L17 | ++++ | ++++ | ++++ | ++++ | + | + |
| L. fructivorans | L19 | +++ | ++++ | ++++ | ++++ | ++ | ++ |
| L. curvatus | L20 | +++ | ++++ | ++++ | ++++ | ++ | ++ |
| L. casei | L22 | +++ | + | − | ++++ | ++++ | ++ |
| Lactobacillus sp. | L137 | − | ++++ | ++++ | ++++ | ++++ | +++ |
| Lactobacillus sp. | L174 | ++++ | − | ++++ | +++ | ++++ | ++ |

TABLE 2-continued

| Pediococcus and Lactobacillus Dot Blot Hybridization Results | | | | | | | |
|---|---|---|---|---|---|---|---|
| Lactobacillus sp. | L176 | ++++ | ++ | − | ++++ | ++++ | ++ |
| Lactobacillus sp. | L177 | ++++ | ++ | − | ++++ | ++++ | ++ |
| Lactobacillus sp. | L178 | +++ | ++++ | ++++ | ++++ | +++ | +++ |
| Lactobacillus sp. | L179 | ++++ | − | ++++ | ++++ | ++++ | + |
| Lactobacillus sp. | L185 | ++++ | ++++ | ++++ | ++++ | ++ | ++ |
| Lactobacillus sp. | L193 | ++++ | ++++ | ++++ | ++++ | ++ | ++ |
| Lactobacillus sp. | L194 | ++++ | ++++ | ++++ | + | ++++ | ++ |
| Spoilage isolate 1 | PedioC4908 | ND | ++++ | ++++ | ++++ | ++++ | ND |
| Spoilage isolate 2 | Pedio53454 | ND | ++++ | ++++ | ++++ | ++++ | ND |
| Spoilage isolate 3 | PedioC30655 | ND | ++++ | ++++ | ++++ | ++++ | ND |
| Spoilage isolate 4 | PedioC3303F | ND | ++++ | ++++ | ++++ | +++ | ND |
| Spoilage isolate 5 | Pedio6667 | ND | ++++ | ++++ | ++++ | ++++ | ND |
| Spoilage isolate 7 | B6665 | ND | ++++ | ++++ | ++++ | +++ | ND |
| Spoilage isolate 8 | LactoC5884B | ND | ++++ | ++++ | ++++ | +++ | ND |
| Spoilage isolate 9 | Lacto53453 | ND | ++++ | ++++ | ++++ | +++ | ND |
| Spoilage isolate 11 | LactoC5884A | ND | ++++ | ++++ | ++++ | +++ | ND |
| Spoilage isolate 13 | LactoC5162 | ND | ++++ | ++++ | ++++ | +++ | ND |
| Spoilage isolate 14 | C4908 | ND | ++++ | ++++ | ++++ | ++++ | ND |
| Spoilage isolate 15 | LactoC3325 | ND | ++++ | ++++ | ++++ | +++ | ND |
| Spoilage isolate 10 | Lacto small | ND | ++++ | ++++ | ++++ | ++++ | ND |
| Spoilage isolate 12 | Lacto large | ND | ++++ | ++++ | ++++ | ++++ | ND |
| Spoilage isolate D | L. brevis GT4696 | ND | ++++ | ++++ | ++++ | ++++ | ND |
| Spoilage isolate A | L. casei GT4697 | ND | ++++ | − | ++++ | ++++ | ND |
| Spoilage isolate F | L. brevis GT4698 | ND | ++++ | +++ | ++++ | ++++ | ND |
| Spoilage isolate B | L. casei GT4699 | ND | ++++ | + | ++++ | ++++ | ND |
| Spoilage isolate | L. brevis GT4700 | ND | ++++ | ++++ | ++++ | ++++ | ND |
| Spoilage isolate J | L. brevis GT4702 | ND | ++++ | + | ++++ | ++++ | ND |
| Spoilage isolate J | L. brevis GT4703 | ND | ++++ | ++++ | ++++ | ++++ | ND |
| Spoilage isolate | L. brevis GT4704 | ND | ++++ | ++++ | ++++ | ++++ | ND |
| Spoilage isolate | L. delbrueckii GT4705 | ND | − | ++++ | ++++ | ++++ | ND |
| Spoilage isolate 852 | L. fructivorans | ND | ++++ | ++++ | ++++ | ++++ | ND |
| Spoilage isolate 853 | L. fructivorans | ND | ++++ | ++++ | ++++ | ++++ | ND |
| L. acidophilus | ATCC4356 | − | − | − | ++++ | − | ++ |
| L. brevis | ATCC8291 | +++ | ++++ | ++++ | ++++ | ++++ | ++ |
| L. buchneri | ATCC11305 | +++ | − | ++++ | ++++ | − | ++++ |
| L. casei | ATCC393 | ++++ | + | − | ++++ | +++ | ++ |
| L. casei ssp. rhamnosus | ATCC7469 | ++++ | + | − | ++++ | ++++ | ++ |
| L. delbrueckii ssp. bulgaricus | ATCC11842 | − | − | − | ++++ | − | − |
| L. fermentum | ATCC9338 | − | ++++ | − | ++++ | +++ | + |
| L. minutus | ATCC33267 | − | − | − | − | − | − |
| L. plantarum | ATCC8014 | ++ | ++++ | ++++ | +++ | + | + |
| L. plantarum | ATCC14917 | ++++ | ++++ | ++++ | +++ | + | + |
| Leuconostoc sp. | Leuco192 | − | − | − | ++ | − | − |
| Leuco. mesenteroides | ATCC8293 | − | − | − | ++ | − | − |
| Acetobacter aceti | ATCC15973 | − | − | − | ++ | − | − |
| Acetobacter aceti | ATCC23746 | − | − | − | ++ | − | − |
| Acetobacter aceti | ATCC23747 | − | − | − | ++ | − | − |
| Acetobacter aceti | ATCC23748 | − | − | − | ++ | − | − |
| Aceto. hansenii | ATCC35959 | − | − | − | ++ | − | − |
| Aceto. liqufaciens | ATCC14835 | ND | ND | ND | ND | ND | ND |
| Aceto. pasteurianus | ATCC12877 | − | − | − | ++ | − | − |
| Aceto. pasteurianus | ATCC12879 | − | − | − | ++ | − | − |
| Aceto. pasteurianus | ATCC23650 | − | − | − | ++ | − | − |
| Aceto. pasteurianus | ATCC23758 | − | − | − | ++ | − | − |
| Aceto. pasteurianus | ATCC23764 | − | − | − | ++ | − | − |
| Aceto. pasteurianus | ATCC23765 | − | − | − | ++ | − | − |
| Aceto. pasteurianus | ATCC23766 | − | − | − | ++ | − | − |
| Aceto. pasteurianus | ATCC23767 | − | − | − | ++ | − | − |
| Aceto. pasteurianus | ATCC33445 | − | − | − | ++ | − | − |
| Bacillus coagulans | ATCC7050 | ++ | − | ++++ | ++ | − | + |
| B. stearothermophilus | ATCC12980 | ND | ND | ND | ND | ND | ND |
| B. subtilis | ATCC21556 | ++++ | − | ++++ | + | − | + |
| Citrobacter freundii | ATCC8090 | − | − | − | − | − | − |
| Enterobacter aerogenes | ATCC13048 | − | − | − | − | − | − |
| E. agglomerans | ATCC27155 | − | − | − | − | − | − |
| E. cloacae | ATCC13047 | − | − | − | − | − | − |
| Flavobacterium ferrugineum | ATCC13524 | − | − | − | ++ | − | − |
| Gluconobacter oxydans | ATCC11894 | − | − | − | ++ | − | − |
| G. oxydans | ATCC19357 | − | − | − | ++ | − | − |
| G. oxydans | ATCC23755 | − | − | − | ++ | − | − |
| G. oxydans | ATCC33446 | − | − | − | ++ | − | − |
| G. oxydans | ATCC33447 | − | − | − | ++ | − | − |
| Hafnia alvei | ATCC13337 | − | − | − | − | − | − |
| Klebsiella oxytoca | ATCC13182 | − | − | − | − | − | − |
| Kleb. terrigena | ATCC33257 | − | − | − | − | − | − |

TABLE 2-continued

Pediococcus and Lactobacillus Dot Blot Hybridization Results

| | | | | | | | |
|---|---|---|---|---|---|---|---|
| *Lactococcus lactis* ssp. *lactis* | ATCC19435 | − | − | ++++ | ++++ | − | − |
| *Megasphaera cerevisiae* | ATCC43236 | ND | ND | ND | ND | ND | ND |
| *Megasphaera cerevisiae* | ATCC43254 | ND | ND | ND | ND | ND | ND |
| *Micrococcus kristinae* | ATCC27570 | − | − | +++ | +++ | − | − |
| *Micrococcus varians* | ATCC15306 | − | − | +++ | +++ | − | − |
| *Obesumbacterium proteus* | ATCC12841 | − | − | − | − | − | − |
| *Pectinatus cerevisiiphilus* | ATCC29359 | − | − | − | ++++ | − | − |
| *Pectinatus frisingensis* | ATCC33332 | − | − | − | ++++ | − | − |
| *Proteus mirabilis* | ATCC29906 | − | − | − | − | − | − |
| *Serratia marcescens* | ATCC13880 | − | − | − | − | − | − |
| *Staphylococcus epidermidis* | ATCC14990 | − | − | ++++ | − | − | + |
| *Staph. saprophyticus* | ATCC15305 | − | − | ++++ | − | − | + |
| *Zymomonas mobilis* | ATCC31821 | ND | ND | ND | ND | ND | ND |
| *Saccharomyces cerevisiae* | ATCC18824 | − | − | − | − | − | − |
| *Saccharomyces cerevisiae* | ATCC2341 | − | − | − | − | − | − |
| *Saccharomyces cerevisiae* | ATCC36902 | − | − | − | − | − | − |
| Chimay | | − | − | − | − | − | − |
| *Candida albicans* | ATCC11006 | − | − | − | − | − | − |
| Human/CaSKi | | − | − | − | − | − | − |
| Stool RNA | | − | − | ++ | ++ | − | − |
| Wheat germ RNA | | − | − | − | − | − | − |

| Probe Organism | Designation | 2875 | 2876 | 2877 | 2896 | 2901 | 2902 |
|---|---|---|---|---|---|---|---|
| | | Pediococcus 23S | | | Pediococcus/Lactobacillus | | |
| *Pediococcus damnosus* | P2 | ++++ | ++++ | ++++ | ++++ | ++++ | ++++ |
| *P. damnosus* | P5 | +++ | ++++ | ++++ | ++++ | ++++ | +++ |
| *P. damnosus* | P10 | ++++ | ++++ | ++++ | ++++ | ++++ | ++++ |
| *P. damnosus* | P17 | ++++ | ++++ | ++++ | ++++ | ++++ | ++++ |
| *P. damnosus* | ATCC29358 | ++++ | ++++ | ++++ | ++++ | ++++ | ++++ |
| *P. pentosaceus* | ATCC33316 | +++ | ++++ | ++++ | +++ | ++++ | − |
| *P. pentosaceus* var. *intermedius* | P18 | − | ++++ | ++++ | − | ++++ | ++++ |
| *Pediococcus* sp. | P140 | − | ++++ | ++++ | − | ++++ | ++++ |
| *Pediococcus* sp. | P160 | − | ++++ | ++++ | − | ++++ | ++++ |
| *Pediococcus* sp. | P167 | − | ++++ | ++++ | − | ++++ | +++ |
| *Pediococcus* sp. | P172 | − | ++++ | ++++ | − | ++++ | ++++ |
| *Lactobacillus delbrueckii* | L4 | − | − | + | − | − | ++++ |
| *L. fructivorans* | L9 | ++++ | − | − | − | ++++ | ++++ |
| *L. casei* | L14 | ++++ | − | − | − | − | − |
| *L. delbrueckii* | L17 | ++++ | − | − | − | ++++ | ++++ |
| *L. fructivorans* | L19 | ++++ | − | − | − | ++++ | ++++ |
| *L. curvatus* | L20 | ++++ | − | − | − | ++++ | ++++ |
| *L. casei* | L22 | ++++ | − | − | − | − | − |
| *Lactobacillus* sp. | L137 | − | ++ | ++ | ++ | ++++ | − |
| *Lactobacillus* sp. | L174 | ++++ | − | − | − | − | − |
| *Lactobacillus* sp. | L176 | ++++ | − | − | − | − | − |
| *Lactobacillus* sp. | L177 | ++++ | − | + | − | − | − |
| *Lactobacillus* sp. | L178 | ++++ | − | − | − | ++++ | ++++ |
| *Lactobacillus* sp. | L179 | ++++ | − | − | − | − | − |
| *Lactobacillus* sp. | L185 | ++++ | − | − | − | ++++ | ++++ |
| *Lactobacillus* sp. | L193 | ++++ | − | − | − | ++++ | ++++ |
| *Lactobacillus* sp. | L194 | ++++ | − | − | − | ++++ | + |
| Spoilage isolate 1 | PedioC4908 | + | ++++ | ++++ | ND | ++++ | ND |
| Spoilage isolate 2 | Pedio53454 | + | ++++ | ++++ | ND | ++++ | ND |
| Spoilage isolate 3 | PedioC30655 | ++++ | ++++ | ++++ | ND | ++++ | ND |
| Spoilage isolate 4 | PedioC3303F | ++++ | − | − | ND | ++++ | ND |
| Spoilage isolate 5 | Pedio6667 | + | ++++ | ++++ | ND | ++++ | ND |
| Spoilage isolate 7 | B6665 | ++++ | − | − | ND | ++++ | ND |
| Spoilage isolate 8 | LactoC5884B | ++++ | − | − | ND | ++++ | ND |
| Spoilage isolate 9 | Lacto53453 | ++++ | − | − | ND | ++++ | ND |
| Spoilage isolate 11 | LactoC5884A | ++++ | − | − | ND | ++++ | ND |
| Spoilage isolate 13 | LactoC5162 | ++++ | − | − | ND | ++++ | ND |
| Spoilage isolate 14 | C4908 | + | ++++ | ++++ | ND | ++++ | ND |
| Spoilage isolate 15 | LactoC3325 | ++++ | − | − | ND | ++++ | ND |
| Spoilage isolate 10 | Lacto small | ++++ | ++++ | ++++ | ND | ++++ | ND |
| Spoilage isolate 12 | Lacto large | ++ | ++++ | +++ | ND | ++++ | ND |
| Spoilage isolate D | *L. brevis* GT4696 | ++++ | − | − | ND | ++++ | ND |
| Spoilage isolate A | *L. casei* GT4697 | ++++ | − | − | ND | + | ND |
| Spoilage isolate F | *L. brevis* GT4698 | ++++ | − | − | ND | +++ | ND |
| Spoilage isolate B | *L. casei* GT4699 | ++++ | − | − | ND | + | ND |
| Spoilage isolate | *L. brevis* GT4700 | + | − | + | ND | + | ND |
| Spoilage isolate J | *L. brevis* GT4702 | ++++ | − | − | ND | + | ND |
| Spoilage isolate J | *L. brevis* GT4703 | ++++ | − | − | ND | ++++ | ND |
| Spoilage isolate | *L. brevis* GT4704 | ++++ | − | − | ND | ++++ | ND |
| Spoilage isolate | *L. delbrueckii* GT4705 | ++++ | − | − | ND | + | ND |

TABLE 2-continued

Pediococcus and Lactobacillus Dot Blot Hybridization Results

| | | | | | | | |
|---|---|---|---|---|---|---|---|
| Spoilage isolate 852 | L. fructivorans | + | ++++ | ++ | ND | ++++ | ND |
| Spoilage isolate 853 | L. fructivorans | + | ++++ | ++ | ND | ++++ | ND |
| L. acidophilus | ATCC4356 | ++++ | – | – | – | – | ++++ |
| L. brevis | ATCC8291 | ++++ | – | – | ++++ | ++++ | ++++ |
| L. buchneri | ATCC11305 | ++++ | – | – | ++ | ++++ | ++++ |
| L. casei | ATCC393 | ++++ | – | – | – | – | – |
| L. casei ssp. rhamnosus | ATCC7469 | +++ | – | – | – | – | – |
| L. delbrueckii ssp. bulgaricus | ATCC11842 | ++++ | – | – | ++ | – | ++ |
| L. fermentum | ATCC9338 | – | + | + | – | ++++ | ++++ |
| L. minutus | ATCC33267 | – | – | – | – | – | – |
| L. plantarum | ATCC8014 | ++++ | – | – | – | ++++ | ++++ |
| L. plantarum | ATCC14917 | ++++ | – | – | – | ++++ | ++++ |
| Leuconostoc sp. | Leuco192 | – | + | – | – | + | – |
| Leuco. mesenteroides | ATCC8293 | – | + | – | – | + | – |
| Acetobacter aceti | ATCC15973 | – | – | – | – | – | +++ |
| Acetobacter aceti | ATCC23746 | – | – | – | – | – | ++ |
| Acetobacter aceti | ATCC23747 | – | – | – | – | – | +++ |
| Acetobacter aceti | ATCC23748 | – | – | – | – | – | +++ |
| Aceto. hansenii | ATCC35959 | – | – | – | – | – | ++ |
| Aceto. liquifaciens | ATCC14835 | ND | ND | ND | ND | ND | ND |
| Aceto. pasteurianus | ATCC12877 | – | – | – | – | – | ++ |
| Aceto. pasteurianus | ATCC12879 | – | – | – | – | – | ++ |
| Aceto. pasteurianus | ATCC23650 | – | – | – | – | – | ++ |
| Aceto. pasteurianus | ATCC23758 | – | – | – | – | – | ++ |
| Aceto. pasteurianus | ATCC23764 | – | – | – | – | – | ++ |
| Aceto. pasteurianus | ATCC23765 | – | – | – | – | – | ++ |
| Aceto. pasteurianus | ATCC23766 | – | – | – | – | – | ++ |
| Aceto. pasteurianus | ATCC23767 | – | – | – | – | – | ++ |
| Aceto. pasteurianus | ATCC33445 | – | – | – | – | – | ++ |
| Bacillus coagulans | ATCC7050 | – | – | – | – | – | – |
| B. stearothermophilus | ATCC12980 | ND | ND | ND | ND | ND | ND |
| B. subtilis | ATCC21556 | – | – | – | – | – | – |
| Citrobacter freundii | ATCC8090 | – | – | – | – | – | – |
| Enterobacter aerogenes | ATCC13048 | – | – | – | – | – | – |
| E. agglomerans | ATCC27155 | – | – | – | – | – | – |
| E. cloacae | ATCC13047 | – | – | – | – | – | – |
| Flavobacterium ferrugineum | ATCC13524 | – | – | – | – | – | – |
| Gluconobacter oxydans | ATCC11894 | – | – | – | – | – | ++ |
| G. oxydans | ATCC19357 | – | – | – | – | – | ++ |
| G. oxydans | ATCC23755 | – | – | – | – | – | ++ |
| G. oxydans | ATCC33446 | – | – | – | – | – | ++ |
| G. oxydans | ATCC33447 | – | – | – | – | – | ++ |
| Hafnia alvei | ATCC13337 | – | – | – | – | – | – |
| Klebsiella oxytoca | ATCC13182 | – | – | – | – | – | – |
| Kleb. terrigena | ATCC33257 | – | – | – | – | – | – |
| Lactococcus lactis ssp. lactis | ATCC19435 | – | – | + | ++ | – | +++ |
| Megasphaera cerevisiae | ATCC43236 | ND | ND | ND | ND | ND | ND |
| Megasphaera cerevisiae | ATCC43254 | ND | ND | ND | ND | ND | ND |
| Micrococcus kristinae | ATCC27570 | – | – | – | – | – | – |
| Micrococcus varians | ATCC15306 | – | – | – | – | – | – |
| Obesumbacterium proteus | ATCC12841 | – | – | – | – | – | – |
| Pectinatus cerevisiiphilus | ATCC29359 | – | – | – | – | – | – |
| Pectinatus frisingensis | ATCC33332 | – | – | – | – | – | – |
| Proteus mirabilis | ATCC29906 | – | – | – | – | – | – |
| Serratia marcescens | ATCC13880 | – | – | – | – | – | – |
| Staphylococcus epidermidis | ATCC14990 | – | + | – | – | – | – |
| Staph. saprophyticus | ATCC15305 | – | + | – | – | – | – |
| Zymomonas mobilis | ATCC31821 | ND | ND | ND | ND | ND | ND |
| Saccharomyces cerevisiae | ATCC18824 | – | – | – | – | – | – |
| Saccharomyces cerevisiae | ATCC2341 | – | – | – | – | – | – |
| Saccharomyces cerevisiae | ATCC36902 | – | – | – | – | – | – |
| Chimay | | – | – | – | – | – | – |
| Candida albicans | ATCC11006 | – | – | – | – | – | – |
| Human/CaSKi | | – | – | – | – | – | – |
| Stool RNA | | – | – | – | – | – | – |
| Wheat germ RNA | | – | – | – | – | – | – |

EXAMPLE 2

Dual Probe Hybridization

For in-process testing, detection of specific spoilage organisms amongst the wide variety of normal brewery microflora might be most appropriate. For this type of sandwich assay, the following capture and detector probe sets are examples of preferred pairs or sets.

P. damnosus 16S rRNA: Probe 2858+Probe 2861 Probe 2861+Probe 2867

*L. brevis* 16S rRNA: Probe 2868+Probe 2869

*P. damnosus* & *L. brevis* 16S rRNA: Probe 2904+Probes 2868+2861

Group of all spoilage 16S rRNA: Probe 2881+Probes 2873+2887

Group of majority of Pediococcus and Lactobacillus 16s rRNA: Probe 2854+Probe 2879

*L. brevis* 23S rRNA: Probe 2880+Probe 2891 Probe 2892+Probe 2895

*P. damnosus* & *L. brevis* 23S rRNA: Probe 2896+Probes 2880+2876

Group of all spoilage 23S rRNA: Probe 2875+Probes 2901+2899

Group of majority of Pediococcus and Lactobacillus 23s rRNA: Probe 2902+Probes 2875+2901.

EXAMPLE 3

Brewery and End-Product Detection of Beer-spoilage organisms

A sample, such as a swab or liquid aliquot from a bottle, can, keg or other container is processed to yield DNA. A probe of this invention is used in conjunction with the antiparallel complement of a second probe of this invention to enzymatically amplify a segment of a target organism gene encoding Lactobacillus rRNA in a polymerase chain reaction. Resultant material is then assayed in a sandwich assay. The polymerase chain reaction can, itself be made either highly specific by employing probe/primers described herein, or the reaction may be made more general using probes such as those described in co-pending U.S. Ser. No. 359,158 and then identifying the amplification product as a target organism using a sandwich assay.

For end-product testing, more generally targeted probes might be appropriate since most normal brewery microflora should have been removed or been inactivated. For this particular assay, the following capture detector and detector probes are examples of preferred pairs:

*P. damnosus* 16S rRNA: Probe 2858+Probe 2861 Probe 2861+Probe 2867

EXAMPLE 4

In situ Hybridization as a Cytological Stain

The probes of this invention may be used as a cytological staining reagents. A liquid sample is applied to a microscope slide. After fixation and lysis, hybridization of probes is carried out in situ. For example, Probe 2858 is labelled with a florescent label and used to stain the specimen. If *P. damnosus* is present in the sample, small fluorescent bodies will be visual under a fluorescent microscope.

EXAMPLE 5

Confirmation of Presence of Beer-spoilage Organisms Following Culture

Following a standard cultivation step for Pediococcus/Lactobacillus/beer spoilage organisms such as on modified MRS agar plates (Lawrence et al, 1979, *J. Instit. for Brewing* 85:119) or in liquid culture enrichment, a sample is tested for the presence of Pediococcus/Lactobacillus/beer spoilage organisms. One method is by use of the sandwich assay described in Example 2. Pure culture is not necessary.

---

What is claimed is:

1. A method of detecting *Pediococcus damnosus* in a sample, said method comprising the steps of
contacting the sample under stringent hybridization conditions with an isolated nucleic acid probe fully complementary to probe 2858 (SEQ ID NO:1), probe 2861 (SEQ ID NO:2), or probe 2867 (SEQ ID NO:3), or the complement of any one of probes 2858, 2861, or 2867, to form a detectable complex with 16S rRNA or rDNA of *Pediococcus damnosus* in the sample, if any, under said stringent hybridization conditions, wherein said probe does not form a detectable complex with rRNA or rDNA of non-*Pediococcus damnosus* bacteria under said stringent hybridization conditions; and
detecting the complexes as an indication of *Pediococcus damnosus* in the sample.

2. A method of claim 1, wherein said probe is probe 2858 (SEQ ID NO:1) or the complement of probe 2858.

3. A method of claim 1, wherein said probe comprises one or more of a detection ligand, an end cap, or a homopolymeric nucleotide sequence.

4. A method of claim 1, wherein said probe comprises an amplifiable Q-beta midivariant nucleotide sequence.

5. A method of detecting *Lactobacillus brevis* in a sample, said method comprising the steps of
contacting the sample under stringent hybridization conditions with an isolated nucleic acid probe fully complementary to probe 2868 (SEQ ID NO:6), 2869 (SEQ ID NO:7), 2880 (SEQ ID NO:8), 2891 (SEQ ID NO:9), 2892 (SEQ ID NO:10), or 2895 (SEQ ID NO:11), or the complement of any one of probes 2868, 2869, 2880, 2891, 2892, or 2895, to form a detectable complex with 16S or 23S rRNA or rDNA of *Lactobacillus brevis* in the sample, if any, under said stringent hybridization conditions, wherein said probe does not form a detectable complex with rRNA or rDNA of non-*Lactobacillus brevis* bacteria under said stringent hybridization conditions; and
detecting the complexes as an indication of *Lactobacillus brevis* in the sample.

6. A method of claim 5, wherein said probe is selected from the group consisting of probe 2869 (SEQ ID NO:7) or the complement of probe 2869.

7. A method of claim 5, wherein said probe comprises one or more of a detection ligand, an end cap, or a homopolymeric nucleotide sequence.

8. A method of claim 5, wherein said probe comprises an amplifiable Q-beta midivariant nucleotide sequence.

9. A method of detecting Lactobacillus or Pediococcus bacteria that cause beer spoilage in a sample of beer, said method comprising the steps of
contacting the sample under stringent hybridization conditions with an isolated nucleic acid probe fully complementary to probe 2876 (SEQ ID NO:4), 2877 (SEQ ID NO:5), 2899 (SEQ ID NO:12), 2904 (SEQ ID NO:13), 2896 (SEQ ID NO:14), 2873 (SEQ ID NO:15), 2887 (SEQ ID NO:17), 2875 (SEQ ID NO:18), or 2901 (SEQ ID NO:19), or the complement of any one of probes 2876, 2877, 2899, 2904, 2896, 2873, 2887, 2875, and 2901, to form a detectable complex with 16S or 23S rRNA or rDNA of Lactobacillus or Pediococcus in the sample, if any, under said stringent hybridization conditions, wherein said probe does not form a detectable complex with rRNA or rDNA of non-Lactobacillus or non-Pediococcus bacteria under said stringent hybridization conditions; and
detecting the complexes as an indication of Lactobacillus or Pediococcus that cause beer spoilage in the sample.

10. A method of claim 9, wherein said probe is probe 2873 (SEQ ID NO:15) or the complement of probe 2873.

11. A method of claim 9, wherein said probe comprises one or more of a detection ligand, an end cap, or a homopolymeric nucleotide sequence.

12. A method of claim 9, wherein said probe comprises an amplifiable Q-beta midivariant nucleotide sequence.

13. A method of claim 5, wherein said probe is probe 2891 (SEQ ID NO:9) or the complement of probe 2891.

14. A method of claim 9, wherein said probe is probe 2876 (SEQ ID NO:4) or the complement of probe 2876.

15. A method of claim 9, wherein said probe is probe 2899 (SEQ ID NO:12) or the complement of probe 2899.

16. A method of claim 9, wherein said probe is probe 2875 (SEQ ID NO:18) or the complement of probe 2875.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:1:

TCACAGCCTT GGTGAGCCTT TATCTCAT    2 8

( 2 ) INFORMATION FOR SEQ ID NO:2:

( i ) SEQUENCE CHARACTERISTICS:

( A ) LENGTH: 29 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:2:

CACTGCATGA GCAGTTACTC TCACACACT      29

( 2 ) INFORMATION FOR SEQ ID NO:3:

( i ) SEQUENCE CHARACTERISTICS:
            ( A ) LENGTH: 28 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:3:

CGGCTAGCTC CCGAAGGTTA CTCCACCT      28

( 2 ) INFORMATION FOR SEQ ID NO:4:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:4:

CCACAGTCTC GGTAATATGT TTAAGCCCCG GT      32

( 2 ) INFORMATION FOR SEQ ID NO:5:

( i ) SEQUENCE CHARACTERISTICS:
            ( A ) LENGTH: 31 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:5:

CGCTCCAACA GTCCTCACGG TCTGCCTTCA T      31

( 2 ) INFORMATION FOR SEQ ID NO:6:

( i ) SEQUENCE CHARACTERISTICS:
            ( A ) LENGTH: 28 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:6:

CAACGTCTGA ACAGTTACTC TCAAACGT      28

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:7:

```
CCGATGTTAA AATCCGTGCA AGCACTTCAT TT                              32
```

( 2 ) INFORMATION FOR SEQ ID NO:8:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:8:

```
TGAGGGTTAT TGGTTTCGTT TACGGGGCTA T                               31
```

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:9:

```
CAGGCTTCCC AACCTGTTCA ACTACCAACA ACT                             33
```

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:10:

```
CCACAATTTG GTGGTATCCT TAGCCCCGGT                                 30
```

( 2 ) INFORMATION FOR SEQ ID NO:11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:11:

CAACCCGGCT GCCAGCATTT AACTGGTAAC CT  32

( 2 ) INFORMATION FOR SEQ ID NO:12:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i i ) HYPOTHETICAL: NO ( i v ) ANTI-SENSE: NO ( x i ) SEQUENCE DESCRIPTION: SEQ ID NO:12:

TCGGTGGATC AGATTCTCAC TGATCTTTCG CT  32

( 2 ) INFORMATION FOR SEQ ID NO:13:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i i ) HYPOTHETICAL: NO ( i v ) ANTI-SENSE: NO ( x i ) SEQUENCE DESCRIPTION: SEQ ID NO:13:

CCAACACTTA GCATTCATCG TTTACGGCAT  30

( 2 ) INFORMATION FOR SEQ ID NO:14:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i i ) HYPOTHETICAL: NO ( i v ) ANTI-SENSE: NO ( x i ) SEQUENCE DESCRIPTION: SEQ ID NO:14:

TTCGCTACGG CTCCGTTTTT TCAACTTAAC CT  32

( 2 ) INFORMATION FOR SEQ ID NO:15:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i i ) HYPOTHETICAL: NO ( i v ) ANTI-SENSE: NO ( x i ) SEQUENCE DESCRIPTION: SEQ ID NO:15:

CCCCTGCTTC TGGGCAGGTT ACCCACGT  28

( 2 ) INFORMATION FOR SEQ ID NO:16:

( i ) SEQUENCE CHARACTERISTICS:
  ( A ) LENGTH: 28 base pairs
  ( B ) TYPE: nucleic acid (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:16:

TCGCTACCCA TGCTTTCGAG CCTCAGCT 28

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:17:

CGCCGCGGGT CCATCCAGAA GTGATAGCCT 30

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:18:

CTGAATTCAG TAACCCTAGA TGGGCCCCTA GT 32

(2) INFORMATION FOR SEQ ID NO:19:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:19:

TATCACTCAC CGTCTGACTC CCGGATATAA AT 32

(2) INFORMATION FOR SEQ ID NO:20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:20:

TAGTTAGCCG TGGCTTTCTG GTTGGAT 27

( 2 ) INFORMATION FOR SEQ ID NO:21:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:21:

CGATTACCCT CTCAGGTCGG CTACGTAT 28

( 2 ) INFORMATION FOR SEQ ID NO:22:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:22:

TTCGGGCCTC CAGTGCGTTT TACCGCACCT T 31